United States Patent [19]

Young et al.

[11] Patent Number: 5,512,485

[45] Date of Patent: *Apr. 30, 1996

[54] HEMATOLOGY CONTROL COMPOSITION INCLUDING LEUKOCYTE ANALOGS; AND METHODS FOR THEIR PREPARATION AND USE

[75] Inventors: Carole Young, Miami; Michael N. Elliott, Cooper City, both of Fla.; Timothy J. Fischer, Raleigh, N.C.; Nancy R. Naylor, Miramar, Fla.

[73] Assignee: Coulter Corporation, Miami, Fla.

[ * ] Notice: The term of this patent shall not extend behyond the expiration date of Pat. No. 5,320,964.

[21] Appl. No.: 342,997

[22] Filed: Nov. 21, 1994

Related U.S. Application Data

[63] Continuation of Ser. No. 182,885, Jan. 14, 1994, abandoned, which is a continuation of Ser. No. 81,752, Jun. 23, 1993, Pat. No. 5,320,964, which is a continuation of Ser. No. 840,435, Feb. 24, 1992, abandoned.

[51] Int. Cl.$^6$ .................................................. G01N 19/00
[52] U.S. Cl. ........................... 436/10; 436/11; 436/15; 436/16; 436/17; 436/18
[58] Field of Search ................................. 436/10, 11, 15, 436/16, 17, 18; 435/2; 252/408.1

[56] References Cited

U.S. PATENT DOCUMENTS

| | | | |
|---|---|---|---|
| 3,741,875 | 6/1973 | Ansley et al. | 436/10 |
| 3,873,467 | 3/1975 | Hunt | 252/408 |
| 4,219,440 | 8/1980 | Runck et al. | 252/408 |
| 4,324,686 | 4/1982 | Mundschenk | 252/408 |
| 4,358,394 | 11/1982 | Crews et al. | 252/408 |
| 4,485,175 | 11/1984 | Ledis et al. | 436/63 |
| 4,579,824 | 4/1986 | Louderback et al. | 436/10 |
| 4,704,364 | 11/1987 | Caver et al. | 436/10 |
| 4,751,179 | 6/1988 | Ledis et al. | 435/34 |
| 4,777,139 | 10/1988 | Wong et al. | 436/18 |
| 5,320,964 | 6/1994 | Young et al. | 436/10 |
| 5,380,664 | 1/1995 | Carver et al. | 436/10 |

*Primary Examiner*—N. Bhat
*Attorney, Agent, or Firm*—Mitchell E. Alter

[57] ABSTRACT

A hematology control product comprising leukocyte analogs is described. The analogs comprise red blood cells which simulate at least two physical properties of human leukocytes. A method for making leukocyte analogs from blood cells having desired physical properties is also described. The process comprises expanding the cell volume, changing the hemoglobin content of the cell and fixing the cell. Generally, the monocyte and lymphocyte analogs leak hemoglobin from the cell while the eosinophil analog has the hemoglobin precipitated in the cell. A further method is described to use the control product to determine whether an automatic instrument is operating within manufacturer's specification.

15 Claims, No Drawings

HEMATOLOGY CONTROL COMPOSITION INCLUDING LEUKOCYTE ANALOGS; AND METHODS FOR THEIR PREPARATION AND USE

This is a continuation of application(s) Ser. No. 08/182,885, filed Jan. 14, 1994, which is a continuation of Ser. No. 08/081,752, filed Jun. 23, 1993, now U.S. Pat. No. 5,320,964, issued Jun. 14, 1994, which is a continuation of Ser. No. 07/840,435, filed Feb. 24, 1992, now abandoned.

FIELD OF INVENTION

This invention relates to reference blood cell analogs for devices using electronic and optical means, suspension media therefor, and processes for making and using the analogs and suspension media in a control product.

BACKGROUND OF THE INVENTION

Quality control long has been a necessary and routine procedure in clinical hematology. Accuracy in the counting of red blood cells and white blood cells, including differentiating among the subpopulations of white blood cells is dependent, in part, upon the use of adequate control products. With the numerous types of equipment for particle counting now available, quality control by the use of control products is necessary, since the possibility of malfunctioning of the instrument is ever present. The traditional method of maintaining a quality control program for automatic particle counting equipment has consisted of providing fresh human blood as a whole blood standard. However, this fresh blood is usable for only one day, therefore, durable blood products were developed.

Hematology control products, which contain reference blood cell analogs, which monitor the accuracy and precision of blood cell counting devices are especially important. It is recognized that there is a present need for new reference blood cell analogs for maintaining the accuracy of white cell differentiation and other parameters when employing such blood cell counting devices.

Control products should approximate that of fresh whole blood as closely as possible. Attempts have been made to provide suitably sized particles in stable suspensions by the use of ragweed pollen, polystyrene, latex, various organic materials and fixed human red cells. None of these suspensions have proved suitable for use as a control product for white cell differentiation of at least four subpopulations of leukocytes.

The material used for maintaining quality control, hereinafter called a hematology control product or control product, can under specific circumstances be used also to calibrate hematology instruments. For the purposes of this invention, the control product will contain one or more analogs suspended in a liquid media which, when analyzed, simulates at least one physical or biological property of blood which the instrument is capable of analyzing. As used herein, an analog is defined as a particle which simulates at least one physical or biological property of a target population. As such, some automatic machines are able to analyze only certain components of a control product, despite the control product having additional parameter components susceptible to analysis by other machines. Heretofore, no analogs or suspension media have been developed for use in a control product to provide checks for at least four subgroups of leukocytes namely, lymphocytes, monocytes, neutrophils and eosinophils.

It is evident that a control product must accurately indicate, on a comparative basis, what a test sample of fresh blood constitutes with regard to the determinations in question. It is further evident how important it is for the control product to simulate fresh blood, since blood components, such as red blood cells, can hemolyze slowly and undergo changes in size and shape within hours after removal from a blood donor. Similarly, white blood cells suffer degenerative changes.

In general, the process of the prior art for making analogs focused on using red blood cells which had maintained or reduced their original volume prior to fixation. Shrinking or expansion of the cells by manipulating their osmotic environment prior to fixation has had its limitations. Previously, shrinking or swelling non-human erythrocytes more than about 30% to 50% caused excessive cell association or lysis of the cell.

U.S. Pat. No. 3,873,467 to Hunt teaches a hematologic reference control comprising a suspension of washed, stabilized human red blood cells in a nonproteinaceous aqueous suspension fluid that replaces the plasma in human blood. Stability in the reference control is attained by conditioning the cells by the inclusion in the aqueous suspension fluid of materials tending to make the cells assume a spherical shape, without substantial change in the mean cell volume of the cells, as well as imparting to the cells a resistance to the normal tendency of degrading with time. The aqueous suspension fluid furthermore produces an environment for the cells inhibiting biological activity. In a preferred embodiment there is further included in the reference control a minor amount of fixed human red blood cells, processed to have a substantially increased mean cell volume. The fixed cells are resistant to a change in cell volume, and to dissolution under the action of lysing reagents producing lysing of the stabilized cells. The fixed red blood cells in the reference control substitute for the white cell population in human blood.

In U.S. Pat. No. 4,704,364, to Carver, et al., there are disclosed controls for thresholds and additional operational performances for electronic particle counters typified by the COULTER COUNTER® Model S Plus type analyzers. However, there is now a need for a whole blood cell control product for electronic optical particle counters typified by the COULTER® VCS analyzer. The VCS analyzer permits the differentiation of at least four populations of leukocytes.

Any system for automated differential counting of human leukocytes, which distinguishes at least four populations of leukocytes from other cells in the blood on the basis of size range, volume distribution, light scatter range, and electrical opacity and conductivity sensitivities requires that the control product closely simulate the range, distribution and sensitivities characteristics of the respective cells in normal human blood. The problem is to find methods which accurately will produce cells of a given size, volume and light scatter properties, in reproducible quantities sufficient to be commercially available for use in control products for automated electronic optical particle counting instruments.

Human lymphocytes, monocytes, neutrophils, basophils and eosinophils have a specific size distribution range and optical characteristics and which after stabilization (for example with a fixative, such as glutaraldehyde), their responsiveness in a suspension media may not permit proper discrimination. This would result in an inability to evaluate proper instrument operation. Both the upper and lower size limits for each subpopulation of leukocytes should be represented in a reference control product. In addition, the mean cell volume of each leukocyte subpopulation in the control product should approximate that of normal human blood. Moreover, it is necessary that the liquid suspension media used for the control product does not cause significant shrinking or swelling of the cells. Still further, the aging of the control product should not result in deterioration of the volume distribution histogram characteristics or other parameters. A further requirement for the leukocyte analogs in the control product for multi-parameter instruments is that in order to be counted and differentiated, the analog cells in a whole blood control product must not be completely lysed by the lytic reagent.

A variety of media have been used in conjunction with blood cell analogs. In U.S. Pat. No. 4,299,726, a multi-purpose diluent and a media is disclosed. The diluent is used to precondition red blood cells and consists essentially of lactose, sodium azide and a non-ionic surfactant; is pH adjusted and osmolality adjusted. The media is used for a carrier of the whole blood control product and includes lactose, fungicides and antibiotics. It also includes additional components which alter red blood cell membranes, including bile salts and cholic acid derivatives, phenothiazine compounds and the salts thereof having antihistamine properties, and 4-amino-benzoic acid ester derivatives and their salts having local anesthetic properties.

One disadvantage of the prior art medias is that, when used in conjunction with red blood cells and fixed human white blood cells or white blood cell analogs, the control product does not simulate a whole blood sample in instruments which differentiate at least four subpopulations of leukocytes. The specific parameters of the red and white blood cells which it is desirable to measure dictate some of the necessary characteristics of a suitable media for a whole blood reference control product. It is desirable to know the volume of the red cell. Once this measurement is ascertained and the red cells have been counted, the packed cell volume or hematocrit can be computed. Therefore, the suspension media of the control product should be capable of equilibrating and stabilizing the volume of red blood cells in the sample so that its mean cell volume can be measured (MCV).

A control product should also be rendered free of any particulate matter that would perhaps demonstrate interference in lower size thresholds corresponding to that of human platelet size and distribution. Concomitantly, the suspension media would optionally include bacteriostatic agents to prevent the growth of microorganisms after packaging the control product.

Although red blood cells (erythrocytes) and white blood cells (leukocytes) nominally have different sizes, their size ranges tend to overlap, or at least under certain conditions of health could overlap. Moreover, the opacity of these two types of blood cells also may overlap. Erythrocytes and the lymphoid leukocytes unfortunately overlap considerably in cell sizes, and it is not practical to count one in the presence of the other by size discrimination alone. Traditional practice involved the use of a strong lytic reagent that stromatolyses the erythrocytes, reducing them to very small particles or causing membrane solubilization, to eliminate them from being counted; and strips most, if not all, of the cytoplasm from the leukocytes, leaving only their lyse-resistant nuclei to be counted. Since original leukocyte cell volume is drastically affected and reduced to a minimum, only a single leukocyte population is discernible by this older form of blood cell size analysis.

U.S. Pat. No. 3,741,875, Ansley et al., describes a process for obtaining a differential white blood cell count. A cytological fixing agent, which is a monoaldehyde, such as formaldehyde, is added to a blood sample. A hemolyzing agent is added after the fixation step to cause the red blood cells to release their hemoglobin content into solution. Addition of a specific cytochemical substrate, chromogenic precipitating coupling reagent, and pH buffer causes deposition of an insoluble dye in a specific type of cell containing an immobilized enzyme. The solution containing the dyed blood cells then is passed through a photometric counter. Using different specific substrates for different enzymes contained in specific kinds of cells, absolute and relative counts of the different kinds of cells are obtained. The cytological fixing solution utilized only a monoaldehyde. Dialdehydes are stated to be unsuitable, since they cross-link and produce extracellular precipitates.

U.S. Pat. No. 4,485,175, to Ledis, et al., concerns a method and reagent system for three-volume differential determination of lymphocyte, mononuclear, and granulocyte populations of leukocytes, using quaternary ammonium salts as lysing agents and the COULTER COUNTER® Model S Plus automated blood counter, which instrument employs only direct current field excitation.

U.S. Pat. No. 4,751,179 to Ledis, et al. describes a reagent system, including saponin in a lysing reagent and a rapidly active cross-linking agent such as glutaraldehyde as a fixing reagent, which reproducibly affects whole blood to cause the red blood cells to stromatolyze and modifies the leukocytes to generate data to define four distinct clusters for detection and classification by flow analysis .instrumentation. The clusters represent the four major leukocyte types found in blood: lymphocytes, monocytes, neutrophils and eosinophils, thus providing a method of leukocyte differential analysis. According to Ledis, et al., previous methods of flow analysis using D.C. volume, or light scatter at various angles have shown only three clusters of leukocytes, corresponding to lymphocytes, monocytes, and granulocytes. The parameters used by Ledis, et al. for the leukocyte classification include combinations of two or more of DC (Coulter) volume, high frequency (RF) size, Coulter opacity (RF size/DC volume), light scatter at various angular ranges, and fluorescence at various wavelengths of illumination.

Electronic counters which employ the Coulter Principle, first described in U.S. Pat. No. 2,656,508, express a true reflection of particle counts. According to the Coulter Principle, when a particle of microscopic size is suspended in an electrolyte liquid, is passed through an electrical field of small dimensions of an order approaching those of a particle, there will be a momentary change in the field's electric impedance. If the electrical field is excited by a direct (DC) or low frequency current, the electrical change is closely proportional to the volume of the particle. In commercial apparatus, the changes are detected by some suitable means and used to operate counters and analyzers. The analyzers associated with such apparatus classify and size particles into populations based upon particle volume and record the data obtained.

The Coulter Principle invention was expanded materially in U.S. Pat. No. 3,502,974, Coulter, et al., using radio frequency (RF) current in addition to DC current field excitation, to provide not only DC volume information concerning the particle studied, but also information due to the composition and nature of the material constituting the particle. This patent discloses apparatus capable of distinguishing between particles of identical size, but of different material. By generating the particle sensing field by means of both a low frequency or direct current (DC) and radio frequency (RF) current excitation, two or more interrelated output signals can be derived from the passage of a single particle through the electrical field. This is due to the fact that, although the particles, such as blood cells, are nearly always insulators with respect to low frequency or direct current fields, they are capable of carrying or impeding radio frequency current differently from the surrounding electrolyte. This may be due to differences in the dielectric constant in the case of homogeneous particles, or to the sac-like structure in the case of blood cells which have, enclosed in an extremely thin membrane, contents having conductivities different from the electrolyte. Thus, while all the DC current goes around a blood cell, some of the RF current will go through it. The ease with which RF current will go through a particle is a measure of what is termed its "electrical transparency", or simply "transparency", in analogy with light transmission; whereas, a particle's ability to impede RF current is termed its "opacity". In later publications, "opacity" is defined as the RF impedance divided by the DC impedance.

The relative electrical opacity of a particle becomes an identifying feature of the particle contents and hence its particle type for classification purposes. To the extent that different types of particles each possess a different opacity, the difference between them is detectable. However, significantly different particles can possess substantially the same opacity and such particles cannot be classified effectively in this manner. In U.S. Pat. No. 3,836,849, Coulter, et al. taught that it is possible to change selectively the opacity of particle types by treatment of the particles, so that detectable differences result.

The COULTER COUNTER® Model S Plus automated blood cell counter is designed to dilute a sample of whole blood in an isotonic diluent, add a lysing agent, and shortly thereafter begin counting. Thus, a diluent-lysing system must provide erythrocyte lysing kinetics sufficiently rapid to effect complete stromatolysation of the red blood cells (erythrocytes) during the lysing period. In addition, changes in leukocyte volume must be minimal during the data collection step, and ideally should be stable for several minutes.

COULTER Model VCS is a semi-automated analytical instrument that analyzes blood by using DC (Coulter) volume, Coulter opacity and light scatter at various angular ranges. The COULTER Model VCS uses a reagent system to obtain a five part differentiation in the total leukocyte count which provide quantitative analysis of the lymphocyte, monocyte, neutrophil, eosinophil and basophil population. The reagent system includes a quench, added after the weak "acid" lyse, the operation of which is to greatly reduce lytic action on the white cells. Shortly after the quench, the instrument begins measuring the volume, opacity and light scattering characteristics of the remaining white blood cells. The Model VCS must provide erythrocyte lysing kinetics sufficiently rapid to effect complete stromatolysation of the red blood cells during the lysing period while not affecting the leukocyte cells as to their volume, Coulter opacity and light scattering properties. The COULTER COUNTER® instruments, with which this invention can be used, are the VCS, STKS and MAXM. However, the Model S and S-Plus types are not able to differentiate all of the subpopulations of leukocyte analogs of this invention which are in a whole blood control product, but rather can provide a total count of the leukocyte analogs. Certain of the S-Plus types are further able to differentiate two leukocyte subpopulations.

New electronic optical particle counting devices have made it necessary to provide leukocyte analogs and suspension media for a stable whole blood control product which more closely simulates a whole blood sample. Although this Specification will be directed primarily to hematology control product embodiments useful with particle counters of the COULTER® type, it should be understood that the suspension media, analogs and control products disclosed herein, and their methods of use described herein, find wide application with particle counters generally. Accordingly, the term "electronic optical particle counter" should be understood to include, in addition to COULTER COUNTER® instruments, any other type of particle counter which discriminates between particles of various sizes by the use of electronic discriminator circuits ("thresholds") which respond electronically to signals indicative of particle size, mass, volume, opacity or light scatter. COULTER and COULTER COUNTER are Registered Trademarks of Coulter Corporation.

SUMMARY OF INVENTION

This invention relates to a hematology control product for use in a particle counting instrument. The invention provides a novel control product comprising one or more blood cell analogs in a liquid media for use in a variety of instruments, preferably instruments which can distinguish among at least four different leukocyte populations. The control product comprises a treated blood cell which has been treated so that it is resistant to degradation by the lytic reagents used in the hematological test procedures, and wherein said control product simulates at least two physical properties of a human leukocyte, said properties selected from the group comprising volume measured by D.C. current, high frequency (RF) size, opacity and light scatter. More preferably, said control product simulates at least two physical properties of a human leukocyte, said properties comprising light scatter and the property selected from the group comprising volume, size and opacity, The white blood cell analogs are produced by mixing a red blood cell with a hypoosmotic solution to expand the volume of the cell; changing the hemoglobin content of the cell to simulate the light scatter and opacity properties of human leukocyte cells; and, fixing the cell so that it is resistant to degradation by lytic reagents used in the hematological test procedure and said fixed cell having at least two properties selected from the group comprising volume measured by D.C. current, high frequency (RF) size, opacity and light scatter properties similar to human leukocytes. The method for making the eosinophil blood cell analog is similar, but the changing of the hemoglobin content is accomplished by denaturing it in the cell rather than leaking it from the cell. This additional embodiment results in an analog having volume and light scattering characteristics of a human leukocyte.

These unique analogs find particular applicability as hematology control products comprising leukocyte analogs which simulate human white blood cells in instruments which employs light scatter, opacity and volumetric measurements to distinguish among the leukocyte populations.

The invention further relates to a quality control method using a hematology control product which contains at least one leukocyte analog for use in a particle counting instrument. The method comprises placing hematology control product in an automatic instrument, said control product containing at least one leukocyte analog which has been derived from a blood cell which has been treated, and wherein said control product simulates at least two physical properties of a human leukocyte said properties comprising selected from the group comprising volume measured by D.C. current, high frequency (RF) size, opacity and light scatter; measuring said physical properties of the control product; and, reporting the results of such measurement in an automatic instrument to determine if said instrument is functioning within specification.

DETAILED DESCRIPTION OF THE INVENTION

Current multiple white blood cell population analysis requires analogs of specific size and volume increments and specific light scatter characteristics for use as a quality control. Therefore, it is presently necessary to prepare an analog for each of the major leukocyte components including at least the lymphocytes, monocytes, neutrophils, and eosinophils in order to check the threshold settings of electronic optical particle counters. Prior hereto, an increased volume was correlated with an increased light scatter which impeded the making of at least four different populations of leukocyte analogs from other than human white blood cells.

The present invention provides a method to treat blood cells from different sources to match a plurality of threshold settings for many types of blood counting instruments. In the selection of the blood cells, the main limitation is the mean cell volume of the original cells as it relates to the mean cell volume of the desired analog. Without limiting the scope of this invention, specific reference will be made to red blood cells from particular animals, with the understanding that red and white blood cells from other animals may be employed in this invention.

In one embodiment, the present method enables the swelling of red blood cells greater than 50% of their original volume, which provides a wider latitude in the selection of animal cells for producing the desired analogs. In a preferred embodiment, the red blood cells are swollen greater than 75% of their original volume.

For the purpose of a preferred embodiment of this invention, it has been found that fowl red blood cells such as turkey, chicken, duck, and preferably goose red blood cells, lend themselves to an aldehyde stabilization process to produce the smaller lymphocyte analogs. It has also been found that other non-human vertebrates including "fishes", particularly members of the shark family, and reptiles, preferably alligators, have red blood cells in the desired size range which when properly treated yields an analog similar to the larger sizes of the human monocytes, neutrophils and eosinophils. These erythrocytes generally show excellent suspension stability and highly reproducible volume distribution characteristics. However, considerations, such as availability in quantity at reasonable expense, must be considered.

These stabilized leukocyte analog cells provide a satisfactory substitute for human leukocyte cells in a control product. Moreover, the red blood cells are fixed so that they are resistant to degradation by the lytic reagent used in the hematological test procedures when determining the white blood cell parameters in a whole blood control product.

The cells of avians, alligators and nurse sharks, are nucleated, but the presence of a nucleus is neither essential nor detrimental for their use as a substitute for human white blood cells, given the process of this invention which permits a regulated hemolysis of the red blood cell. Preferably between 20% to 80% by weight and most preferably 30% to 70% by weight of the hemoglobin in the cell is released. The cells are further stabilized with a fixing agent, such as an organic aldehyde which prevents disruption of the cell membrane and further loss of hemoglobin.

The present invention further embodies a composition prepared by mixing a suspension of fixed goose red blood cells to simulate human lymphocytes, fixed alligator red blood cells to simulate human monocytes, neutrophils, and eosinophils, all assembled in a suspension media and in such proportions as to provide a single composition to simulate human white blood cells. This leukocyte analog composition then is commingled with lysable human red blood cells, and stabilized platelets or platelet analogs, to provide a single multiple-analysis control product.

In the collecting step, the red blood cells are suspended in an anticoagulant, such as an alkali metal salt of ethylenediaminetetraacetic acid (EDTA) dissolved in a physiological saline solution (sodium chloride). It is envisioned that other anticoagulants and salts will do, as long as they do not cause undue hemolysis or cell association.

Fresh red blood cells must be washed to remove donor specific plasma proteins. This will reduce the probability of cell agglutination when mixing red cells from multiple blood cell donors. The cells are pooled together to obtain a homogeneous composite.

The cell pool may be pretreated with a serum substance as a processing aid. The pretreatment with the serum substance permits swelling of the cell without causing the cell to rupture. Exposure of the erythrocytes to a hypoosmotic environment has the principal effect of increasing the mean corpuscular volume, and decreasing the widths of the light scatter histogram. The blood cells are increased in size as a result of the hypoosmotic environment having a solute concentration which is reduced from the solute concentration of the cells. When the concentration of solute inside the cell is greater than the concentration outside the cell, there is a tendency for the water to move into the cell to equilibrate concentration. As such, the moving of water inside the cell causes swelling. The hypoosmotic environment can include a solution of sodium compounds, potassium compounds, or both sodium and potassium or other compositions known to those skilled in the art to provide the desired solute concentration.

The serum substance comprises an aqueous solution of serum lipid. As defined herein, serum lipid comprises cholesterol, cholesterol esters and cholesterol which has been combined with one or more other compounds found in serum plasma and mixtures thereof. Preferably, such other compounds further comprise lipoproteins and phospholipids, and mixtures thereof. As appreciated by those skilled in the art, typically, cholesterol will contain approximately 30% esters. As further appreciated by those skilled in the art, the lipoprotein will be required to maintain the cholesterol in an aqueous solution. Preferably, the serum substance in the pretreatment is selected from the group comprising cholesterol, cholesterol esters, lipoprotein cholesterol, lipoprotein cholesterol esters, cholesterol combined with phospholipids and mixtures thereof. Most preferably, the serum substance comprises cholesterol in combination with phospholipids. A suitable commercially available example of such most preferred embodiment is pentex® Cholesterol Super-Trate by Miles, Inc., which is a high density lipoprotein cholesterol and lipoprotein cholesterol esters in combination with phospholipids. Thus, when smaller cells are expanded greater than 30% to 50% of their original volume, the pretreatment is necessary. It is further believed that the concentration of the serum substance used is both a function of the amount of cell expansion, caused by the hypoosmotic solution, as well as, the process conditions of the fixation reaction which permits the cell's hemoglobin to leak from the cell. In processes which fix the cell in less than approximately 2. hours due mainly to the aldehyde concentration at room temperature, and wherein the hypoosmotic pressure is greater than approximately 150 milliosmoles, no pretreatment appears necessary. When the pretreatment is used, preferably the concentration of the cholesterol is from 0.1 to 5.0 milligrams to a cell count of $1 \times 10^6$ cells per microliter. If too high of a cholesterol concentration used, then the cells will tend to lyse. If too low of cholesterol concentration is used, the cell will rupture when swelled.

Prior art attempts at swelling cells without bursting them have focused on the use of a processing aid, such as potassium sodium tartrate, which functions to strengthen the cell membrane. However, this approach does not permit expansion greater than the expected 30 to 50%, nor provide the cell with regulated hemolysis.

Although the present invention is disclosed in terms of simultaneously swelling and fixing of the cell in a one step process, it is within the contemplation of this invention that more than one step could be used to pretreat the cell with the serum substance, swell the cell to permit a controlled release of hemoglobin and thereafter fix the cell. However, such procedure would be expected to have the problems of controlling the process conditions for each step, and more specifically, the timing of the fixation of the blood cell.

In a preferred embodiment of the process of this invention, the hypoosmotic solution is formed by combining an aqueous solution of sodium phosphate with the fixative reagent to the desired osmotic pressure. The lower the osmotic pressure relative to the normal tonicity of the native blood, the more that the cell will swell due in part because of the water moving from outside the cell to inside the cell. The osmotic pressure will preferably range from 0 to 150 milliosmoles, depending upon the initial cell size, cell count, and the desired final cell size; even more preferably from 65 to 95 milliosmoles for the eosinophil analog; 0 to 20 milliosmoles for the monocyte analog; 5 to 35 milliosmoles for the lymphocyte analog; and from 45 to 65 milliosmoles for the neutrophil analog. The above preferred ranges are based upon blood cells that have been washed with an isotonic saline solution and are further based upon a cell count in the fixative reaction of approximately 20,000 to 50,000 cells per microliter.

Concomitantly, temperature does not appear to independently affect the swelling rate of the cell, but does affect the rate of the fixation reaction. As the cell expands, the hemoglobin leaks out of the cell at a controlled rate until the fixation reaction prevents further release of hemoglobin. The majority of the hemoglobin will be released within the first five minutes of the hypoosmotic treatment. Thus, in the simultaneous swelling and fixing of the cells, reducing the temperature of the fixation in solution enables the control of the fixation process and hemoglobin release rates during which time the cell is swelling. Upon completion of the fixation reaction, the cell is resistant to dissolution or degradation under the influence of the usual lysing reagents used in hematological test procedures.

In a further preferred embodiment, the blood cells are added to a chilled hypotonic solution containing glutaraldehyde. The chilled fixing solution is at a temperature of 0° to 15° C., and more preferably, from 1° to 10° C. In a most preferred embodiment, the fixation treatment is at 2° to 8° C. for the lymphocyte and monocyte analogs and at room temperature for the neutrophil and eosinophil analogs. The reduced temperature has been shown to provide a qualitatively different cell as measured on a sizing apparatus such as a COULTER COUNTER® Model VCS analyzer. A qualitative difference includes a higher mean cell volume and lower light scatter compared to fixing at room temperature.

Fixing of the swollen cells is important to toughen the cell membranes and to prevent degradation of the membranes. This is accomplished by contacting the cells with a solution of an organic aldehyde, including monoaldehydes such as formaldehyde, or dialdehydes such as glutaraldehyde. Glutaraldehyde is the preferred aldehyde, since it reacts more rapidly than formaldehyde. Glutaraldehyde can be added in higher concentrations than the final concentration, so long as the final concentration is in the range of about 0.05% to 0.8% and more preferably 0.1% to 0.6%, based upon a cell count of approximately 20,000 to 50,000 cells per microliter. The practical limitations on selection of an appropriate aldehyde and concentration thereof are the functional limitations of the number of cells, elimination of undue cell association, and as a parameter in controlling the fixation reaction. The fixation reaction conditions will vary for the specific animal cell used and the leukocyte analog being manufactured.

Although most room temperature fixation with glutaraldehyde occurs within two hours, more time is required for the red blood cells to be totally resistant to the usual red blood cell lytic agents employed in COULTER COUNTER hematology instruments. With careful selection of the red blood cells, the length of time for fixation with glutaraldehyde will range between 2 and 72 hours, preferably between 3 to 30 hours, depending upon temperature, concentration of glutaraldehyde, number of cells and desired amount of hemoglobin released. In a most preferred embodiment, the fixation time for a cell count of approximately 20,000 to 50,000 cells per microliter is between 10 to 24 hours for the monocyte and lymphocyte analogs and 3 to 18 hours for the eosinophil and neutrophil analogs. Under-fixation may result in a partially fixed red blood cell with a mean cell volume less than that for the targeted human leukocyte population. Generally, the upper time limit of fixation is based upon manufacturing convenience. After fixation, the cells are separated from the liquid phase by a centrifugation or gravitation means and then are washed with a phosphate buffered saline solution.

The pH of the fixing solution ranges from 7.0 to 9.0. If the pH of the fixing solution is too low, agglutination may occur; and if too high, the cell may rupture. In addition, the pH affects the release of hemoglobin. If the fixation reaction occurs too quickly, the cell will not be able to leak the hemoglobin. Thus, according to this invention, the pH range is approximately 7.0 to 9.0, and preferably 7.5 to 8.5. In a most preferred embodiment, the pH of the fixation solution is 8.0±2 for the neutrophil and eosinophil analogs, and 7.8±1 for the monocyte and lymphocyte analogs.

The eosinophil analog is prepared in a similar process except, the hypotonic glutaraldehyde solution is preferably at room temperature and the hypotonic glutaraldehyde solution is primarily used to lightly cross link the hemoglobin in the blood cells, rather than to completely fix the cell. As such, the glutaraldehyde concentration for a cell count of approximately 20,000 to 50,000 cells per microliter is between approximately 0.1 and 0.4% and more preferably from 0.2 to 0.3% After lightly cross linking the hemoglobin and washing with a phosphate buffered saline solution, the cells are further treated with a protein denaturing reagent, such as a quaternary ammonium compound, or other denaturing agent known to those skilled in the art to precipitate the hemoglobin within the cell. The pH of the denaturing solution should be between 9.0 and 12.0, and preferably between 10.0 and 11.0. This treatment does not reduce the volume of the cell. The treatment with the protein denaturing reagent increases the light scatter characteristics of the swollen cell to provide the swollen cell with the requisite light scattering characteristics similar to the human eosinophil. Both the denaturation of the hemoglobin and the controlled release of the hemoglobin have the effect of changing the hemoglobin composition in the cell. However, the light scatter properties are distinctly different between the controlled release of the hemoglobin in the monocyte and lymphocyte analogs and the denaturation of hemoglobin in the eosinophil analog. Generally, the leaking of hemoglobin from the cell will reduce the light scatter and opacity of the cell. Denaturing the hemoglobin in the cell will increase the light scatter of the cell.

The preferred method of preparing the eosinophil analog comprises pretreating the red cell pool with an aqueous serum substance, swelling the cell, denaturing the hemoglobin in the cell and fixing the cell. As appreciated by one skilled in the art, it is within the contemplation of this method in that one could choose an appropriate sized red blood cell which did not require the amount of swelling which would necessitate the pretreatment with the serum substance. In such case, the process would comprise denaturing the hemoglobin in the cell to simulate the light scatter properties of a human leukocyte cell and fixing the cell so that it is resistant to degradation by lytic reagents used in hematological test procedures. As such, the treated red cell would have light scatter and volume properties similar to human leukocytes. However, if the cell is not swelled to some extent, it would be expected that since the red blood cell is not by nature spherical, the standard deviation of the light scatter would not be within boundary of the targeted cell population. The addition of a sphering agent may obviate this problem.

By using a combination of the above disclosed processing steps, of swelling the cell, leaking of hemoglobin from the cell, denaturing the hemoglobin in the cell, as well as, shrinking the cell by methods known to those skilled in the art, one is effectively provided with methods to design an analog having a plurality of different physical parameters of D.C. volume, RF size, opacity and light scatter. More specifically, shrinking and swelling of the cell can affect all of the above listed parameters, while changing the hemoglobin in the cell can affect the RF size, opacity and light scatter characteristics.

The reference blood cell control product can include one or more of the leukocyte analogs. The leukocyte analogs can be stored in any suitable suspension media. Examples of such media includes phosphate buffered saline solution and an aqueous solution of a plasma substance. As defined herein, an aqueous solution of a plasma substance comprises an aqueous solution of a serum substance (as previously defined), serum substance in combination with a plasma protein and mixtures thereof. As further defined herein, plasma protein comprises one or more of the proteins contained in plasma. Preferably, such plasma proteins comprise albumin, lipoproteins, globulins, fibrinogens and mixtures thereof. These media may contain other ingredients known to those skilled in the art to confer long term stability. Other examples of suitable media are more fully described in U.S. Pat. Nos. 4,213,876; 4,299,726; 4,358,394 and 3,873,467.

The following specific example is disclosed in U.S. Pat. No. 4,299,726:

Stabilizing Media for Conferring Long Term Stability on Red Blood Cells-Preferred Formulation

| Approximate Amounts | | Liter Formulation |
|---|---|---|
| 1. | Distilled water | 500 ml |
| 2. | Propyl paraben | 0.3 to 1.0 gm |
| 3. | Methyl paraben | 0.5 to 1.0 gm |
| 4. | Procaine hydrochloride | 0.1 to 0.5 gm |
| 5. | Deoxycholic acid | 0.1 to 0.9 gm |
| 6. | Lactose | 10.0 to 50.0 gm |
| 7. | Actidione | 0.1 to 0.6 gm |
| 8. | Trisodium citrate dehydrate | 3.0 to 8.0 gm |
| 9. | Citric acid monohydrate | 0.3 to 0.9 gm |
| 10. | Sodium dihydrogen phosphate monohydrate | 0.8 to 2.5 mg |
| 11. | Phenergan hydrochloride | 0.1 to 1.0 gm |
| 12. | Colistimethate, sodium | 0.2 to 0.9 gm |
| 13. | Penicillin G., sodium | $0.5 \times 10^6$ to $3 \times 10^6$ units |
| 14. | Kanamycin sulfate | 0.2 to 0.8 gm |
| 15. | Neomycin sulfate | 0.2 to 1.0 gm |
| 16. | 5'-AMP | 0.4 to 1.0 gm |
| 17. | Adenine | 0.2 to 0.8 gm |
| 18. | Inosine | 0.4 to 1.0 gm |
| 19. | Dihydrostreptomycin sulfate | 0.2 to 1.0 gm |
| 20. | Tetracycline hydrochloride | 0.2 to 1.0 gm |
| 21. | 30% Bovine albumin | 100 to 350 ml |
| 22. | q.s. to 1 liter with distilled water | |

Since many of the chemicals listed above are known commercially by several names, the name given is a common name listed in the Merck Index, Eleventh Edition (1989), published by Merck and Co., Inc., Rahway, N.J.

Preferably, the control product comprises one or more leukocyte analogs in an aqueous solution of a plasma substance. In a more preferred embodiment of this invention, when one or more leukocyte analogs are combined with lysable human red blood cells to provide a single multiple analysis reference blood cell control product for instruments which use lytic reagents, the plasma substance is selected from the group comprising cholesterol, cholesterol ester, lipoprotein cholesterol, lipoprotein cholesterol esters, cholesterol combined with phospholipid, cholesterol combined with albumin, cholesterol ester combined with albumin, lipoprotein cholesterol combined with phospholipids, lipoprotein cholesterol combined with albumin and mixtures thereof. Most preferably, the plasma substance comprises bound cholesterol. A suitable commercially available example of the most preferred plasma substance is Moducyte®, as described in U.S. Pat. No. 4,290,774, assigned to Miles, Inc., which is a high density lipoprotein cholesterol bound with albumin. The final concentration of cholesterol in the suspension media ranges from 400 to 1,200, and preferably 600 to 1,000 milligrams per liter, depending upon the cell count in the final control product.

If an insufficient concentration of the cholesterol is used in the media of the more preferred embodiment of this invention, the red blood cells in the reference blood cell control product will not efficiently lyse to dissolve the cell membrane so that there is an absence of noise and debris when using a saponin lytic reagent system and the leukocyte analogs will have a mean cell volume below the required size due to the lytic reaction. If the media contains too high of a concentration of cholesterol, the red blood cells in the reference blood cell control will not efficiently lyse to dissolve the cell membrane so that there is an absence of noise and debris.

More specifically, when the more preferred embodiment of the control product is used in instruments, such as those that employ the Coulter Model VCS technology, which uses a reagent system such as described in U.S. Pat. No. 4,751,179, in order to distinguish at least two populations of leukocytes, (1) lymphoids (lymphocytes) and (2) myeloids (neutrophils, monocytes, eosinophils and basophils), the aqueous plasma substance (as previously defined) enables the reaction between the weaker lytic reagent and the non-fixed red blood cells to occur so that the red blood cells lyse while the leukocyte analogs remain substantially unaffected, enabling each type of leukocyte analog to be counted. As taught by U.S. Pat. No. 4,751,179, the lysing reagent has two forms: (1) a lytic diluent containing saponin, which simultaneously functions to dilute the whole blood sample and stromatolyse its red blood cells; or (2) a two part system comprised of non-lytic blood diluent followed by a lytic reagent containing saponin.

When prior art medias, such as those described in U.S. Pat. Nos. 4,213,876; 4,299,726; or 4,358,395, are used with the more preferred embodiment of this invention, the leukocyte analogs prepared by the above described method are lower in volume than desired for the targeted leukocyte population.

In a most preferred embodiment, the suspension media used in the control product would further comprise the addition of a non-ionic surfactant. The surfactant will have a high hydrophile-lipophile balance (HLB). The HLB typically has a value greater than 15 and more preferably greater than 17. Typically, the surfactant is in an amount effective to make the lytic action more specific to the red blood cells without detrimentally affecting the leukocyte analogs. In addition, the surfactant will stabilize any free cholesterol in the control product so that it does not separate out in solution. As appreciated by those skilled in the art, the effective amount of surfactant may be empirically determined, but is typically less than 0.5% by weight of the control product.

Suitable non-ionic surfactants include alkyl polyether alcohols of the general formula: R—X—(y)$_n$—H, where R is a lipophilic chain $C_8$–$C_{18}$ carbon atoms; where X is —O—,

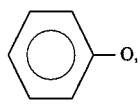

—COO—; and Y is $CH_2$ $CH_2O$— or $CH_2$ $CH_2$ $CH_2O$; n is an integer of 15–50. Suitable commercial examples of these surfactants include Diazopan® SS-837 by GAF Chemical Corp., Triton® X405 by Rohm and Haas, and Pluronic F® -127 PRILL by BASF Wyandotte Corp.

While not desiring to be bound by any theory of the invention, it is presently believed that there is an interaction among the red blood cells, weak lytic agent (e.g., saponin), and the plasma substance in the suspension media which causes the red blood cells to lyse. More specifically, it is presently believed that the plasma substance may be affecting the cell membrane cholesterol which further affects the leukocyte analog's response to the lytic reagent. Moreover, it is further believed that the surfactant makes the lytic reaction more specific to the red blood cells and yet does not detrimentally affect the leukocyte analogs as to measured parameters. In addition, it is further believed that the surfactant may also be affecting the cholesterol found in the cell membrane or in the plasma substance.

The process for preparing leukocyte analogs according to this invention is hereinafter provided in the Examples.

Example 1 is a specific example of preferred reagents and techniques for treating goose cells, it being understood that the formulations are only illustrative. Examples 2, 3 and 4 are specific examples of preferred reagents and techniques for treating the alligator cells, it being understood that the formulations are only illustrative. Example 5 shows an assembly of the four leukocyte populations, it being understood that the formulation is only illustrative. The reagents and/or techniques described can also be applicable to blood cells from animals other than geese and alligators. Other ingredients and proportions can be employed, in accordance with this disclosure.

EXAMPLE 1

Lymphocyte Analog From Goose Red Blood Cells

The following is a specific example of preferred reagents and recommended specific procedural steps for treating goose red blood cells to obtain a normal sized lymphocyte analog. It will be understood that the formulations and the procedures only are illustrative and that other ingredients, proportions and procedures can be employed, in accordance with the disclosures in this invention.

Phosphate Buffered Saline Solution (PBS) Liter Formulation
  1. Sodium phosphate monobasic: 0.2 g
  2. Sodium phosphate dibasic .7H$_2$O:2.0 g
  3. Sodium azide: 0.1 g
  4. Sodium chloride: 9.4 g
  5. q.s. to 1 liter with distilled water: pH approximately 7.4; osmolality 315 to 345 mOsm/kg.

Lymphocyte Hypotonic Solution
  1. Sodium phosphate monobasic: 0.2 g
  2. Sodium phosphate dibasic .7H$_2$O:2.0 g
  3. q.s. to 1 liter with distilled water:pH approximately 7.8; osmolality 15 to 25 mOsm/kg.

Procedure

1. Select avian red blood cells having a mean cell volume range of about 140 to 170 fL. Wash the packed avian red blood cells with the phosphate buffered saline solution (PBS).

2. Add 1.0 to 5.0 milligrams of cholesterol to a cell count of 2×10$^6$ per microliter and incubate for 2 to 6 hours, at room temperature.

3. Prepare a glutaraldehyde fixative reagent having a glutaraldehyde content of about 0.1 to 0.8% by adding a commercial 25% glutaraldehyde product to the chilled Lymphocyte Hypotonic Solution. Preferably, the temperature is from 2° to 8° C. The preferred concentration of glutaraldehyde is approximately 0.35%.

4. Add the washed red blood cells to a measured amount of the fixative of step 3 at a 1:35 dilution. Transfer to sealed containers which are rolled slowly for 18 to 24 hours at 2° to 8° C. The reduction in hemoglobin content is calculated to be approximately 60% by weight.

5. Remove the supernatant fluid, wash cells several times with the PBS, then resuspend in a suitable storing solution.

6. For a stand alone lymphocyte analog, resuspend the washed fixed cells in a suitable suspension media and adjust the concentration to simulate that of human lymphocyte cells in normal human blood.

7. For multiple hematological parameters for a control product, add the washed fixed cells of step 6 with other hematological compositions and analogs desired for the multiple parameter hematology control product, the cell count being appropriate to measure lymphocyte proportions.

8. With suitable stabilizers, the fixed cells can be stored for a time period in excess of six months.

In accordance with the above example, but starting with other types of mammalian red blood cells, comparable results are obtained.

EXAMPLE 2

Monocyte Cell Analog From Alligator Red Blood Cells

The following is a specific example of preferred reagents and recommended specific procedural steps for treating alligator red blood cells to obtain the monocyte cell analog. It will be understood that the formulations and the procedures are only illustrative and that other ingredients, proportions and procedures may be employed, in accordance with the disclosures in this invention.

Monocyte Hypotonic Solution

1. Sodium phosphate monobasic: 0.1 g
2. Sodium phosphate dibasic 1.0 g
3. q.s. to 1 liter with distilled water; pH approximately 7.8; osmolality 5 to 15 mOsm/kg.

Washing solution for cells (PBS), as set forth in Example 1.

Procedure

1. Select alligator red blood cells having a mean cell volume range of about 350 to 450 fL. Wash the packed alligator red blood cells with PBS.
2. Add 1.0 to 5.0 milligrams of cholesterol to a cell count of $1\times10^6$ per microliter and incubate 3 to 5 hours at room temperature.
3. Prepare a glutaraldehyde fixing reagent having a glutaraldehyde content of about 0.1 to 0.8% by adding a commercial 25% glutaraldehyde product to the chilled Monocyte Hypotonic Solution. Preferably the temperature is from 2° to 8° C. The preferred concentration of glutaraldehyde is approximately 0.15%.
4. Add the washed red blood cells to a measured amount of the fixative of step 3 at a 1:50 dilution. Transfer to sealed containers which are rolled slowly for 18 to 24 hours at room temperature. The reduction in hemoglobin content is calculated to be approximately 40% by weight.
5. Remove the supernatant fluid, wash cells several times with the PBS, then resuspend in a suitable storing solution.
6. For a stand alone monocyte analog, resuspend the washed fixed cells in a suitable suspension media and adjust the concentration to simulate that of human monocyte cells in normal human blood.
7. For multiple hematological control product, add the washed fixed cells of step 6 with other hematological compositions and analogs desired for the multiple parameter control product in the appropriate concentration to measure monocyte cells.
8. With suitable stabilizers, the fixed cells can be stored for a time period in excess of six months.

EXAMPLE 3

Eosinophil Analog From Red Blood Cells of the Alligator

The following is a specific example of preferred reagents and recommended specific procedural steps for treating red blood cells of the alligator to obtain the eosinophil analog. It will be understood that the formulations and the procedures are only illustrative, and that other ingredients, proportions and procedures may be employed, in accordance with the disclosures in this invention.

Eosinophil Hypotonic Solution

1. Sodium phosphate monobasic: 0.32 grams
2. Sodium phosphate dibasic 8.08 grams
3. q.s. to 1 liter with distilled water; pH approximately 8.0; osmolality 75 to 85 mOsm/kg.

Eosinophil Hemoglobin Denaturing Treatment Solution 1. dimethyldicocoammonium chloride 2.5 grams
2. tris(hydroxymethyl)amino methane 6.06 grams (organic buffer)
3. q.s. to 1 liter with distilled water: pH approximately 10.5.

Eosinophil Post-Treatment Wash Solution 1. polyoxethylated alkylphenol 5 grams (Diazopan® SS-837 by GAF Chemical Corp.)
2. q.s. to 1 liter with distilled water Washing solution for cells (PBS), as set forth in Example 1.

Procedure

1. Select alligator red blood cells having a mean cell volume range of about 400 to 500 fL. Wash the packed alligator red blood cells with PBS.
2. Add 0.25 to 1.25 milligrams of cholesterol to a cell count of $1\times10^6$ per microliter and incubate 2 to 5 hours, at room temperature.
3. Prepare a glutaraldehyde cross linking reagent having a glutaraldehyde content of about 0.1 to 0.8% by adding a commercial 25% glutaraldehyde product to the Eosinophil Hypotonic Solution. The preferred concentration of glutaraldehyde is approximately 0.2%.
4. Add the washed red blood cells to a measured amount of the cross linking of step 3 at a 1:50 dilution. Transfer to sealed containers which are rolled slowly for 18 to 24 hours at room temperature.
5. Remove the supernatant fluid, wash cells several times with the PBS.
6. Add the washed red blood cells to the Eosinophil Hemoglobin Denaturing Treatment Solution at a 1:10 dilution. Transfer to sealed containers which are rolled slowly for 2–4 hours at room temperature.
7. Remove the supernatant fluid, wash cells several times with the Eosinophil Post-Treatment Wash Solution to remove the Eosinophil Hemoglobin Denaturing Treatment Solution. Then resuspend in a suitable storage solution.
8. For a stand alone eosinophil analog, resuspend the washed fixed cells in a suitable suspension media and adjust the concentration to simulate that of human eosinophil cells in normal human blood.
9. For multiple hematological control products, add the washed fixed cells of step 8 with other hematological compositions and analogs desired for the multiple parameter control product in the appropriate concentration to measure eosinophil cells.
10. With suitable stabilizers, the fixed cells can be stored for a time in excess of six months.

EXAMPLE 4

Neutrophil Cell Analog From Alligator Red Blood cells

The following is a specific example of preferred reagents and recommended specific procedural steps for treating alligator red blood cells to obtain the monocyte cell analog. It will be understood that the formulations and the procedures are only illustrative and that other ingredients, proportions and procedures may be employed, in accordance with the disclosures in this invention.

Neutrophil Hypotonic Solution

1. Sodium phosphate monobasic: 0.23 g
2. Sodium phosphate dibasic 5.32 g 3. q.s. to 1 liter with distilled water; pH approximately 8.0; osmolality 45 to 65 mOsm/kg.

Washing solution for cells (PBS), as set forth in Example 1.

Procedure

1. Select alligator red blood cells having a mean cell volume range of about 400 to 500 fL. Wash the packed alligator red blood cells with PBS.

2. Prepare a glutaraldehyde fixing reagent having a glutaraldehyde content of about 0.1 to 0.8% by adding a commercial 25% glutaraldehyde product to the Neutrophil Hypotonic Solution. The preferred concentration of glutaraldehyde is approximately 0.4%.

3. Add the washed red blood cells at a count of $1 \times 10^6$ to a measured amount of the fixative of step 3 at a 1:50 dilution. Transfer to sealed containers which are rolled slowly for 18 to 24 hours at room temperature.

4. Remove the supernatant fluid, wash cells several times with the PBS, then resuspend in a suitable storing solution.

5. Add packed cells to a nonionic surfactant solution. Said solution tends to standardize the volume of donor cells. The solution comprises 0.5 grams of octylphenoxy polyethoxy ethanol having an HLB of approximately 13.5 (Triton® X-100 by Rohm and Haas Co.,) in 1 liter of distilled water.

6. Remove the supernatant fluid, wash cells several times with the PBS, then resuspend in a suitable storing solution.

7. For a stand alone neutrophil analog, resuspend the washed fixed cells in a suitable suspension media and adjust the concentration to simulate that of human neutrophil cells in normal human blood.

8. For multiple hematological control product, add the washed fixed cells of step 7 with other hematological compositions and analogs desired for the multiple parameter control product in the appropriate concentration to measure neutrophil cells.

9. With suitable stabilizers, the fixed cells can be stored for a time period in excess of six months.

EXAMPLE 5

In a sub-assembly for simulating the targeted composition of white blood cells in a normal human blood sample, the following quantities of the individual components are employed:

| | | | STOCK SOLUTION |
|---|---|---|---|
| 0.150 L | Example 1 | lymphocytes | $500 \times 10^3$/uL |
| 0.040 L | Example 2 | monocytes | $500 \times 10^3$/uL |
| 0.030 L | Example 3 | eosinophils | $500 \times 10^3$/uL |
| 0.280 L | Example 4 | neutrophils | $500 \times 10^3$/uL |
| 0.500 L | diluent | phosphate buffered saline | |

In the final assembly of the four leukocyte populations, remove the supernatant fluid, then resuspend the cells in 1.0 liter of an aqueous solution of Moducyte® having a final concentration of 800 milligrams of cholesterol.

This assembly can be stored for up to about six months with the addition of known suitable stabilizers.

The ratio and total cell count for the leukocyte populations can be adjusted to represent pathological, as well as normal conditions in human blood. These compositions are useful likewise in control and calibrator products particularly for automated particle analysis instruments employing the Coulter Principle.

Suspensions of untreated human red blood cells, simulated white blood cells, and stabilized or Simulated platelets can be thereafter added in such proportion that the final red blood cell, white blood cell and platelet counts, as well as hemoglobin content and hematocrit fall in the desired range.

Stabilized platelets are furnished by methods known in the art. Useful methods include:

1. A combination of iodoacetamide and an iminodiacetic acid or salt thereof, together with a compatible bacteriostatic agent in an aqueous solution which is maintained at a preselected range of pH and osmolality as is described in U.S. Pat. No. 4,405,719.

2. A fixative-stabilizing composition containing a glutaraldehyde concentration of 0.1% to 5% and a nonionic surfactant which is a mixture of ethoxylates of certain isomeric linear alcohols, as is more fully described in U.S. Pat. No. 4,389,490.

3. A human platelet analog comprising goat erythrocytes stabilized, combined and blended as necessary to have a size range and volume distribution close to that of human platelets, as is described in U.S. Pat. No. 4,264,470.

The values for each of the hematological parameters can be varied to represent abnormal low and abnormal high conditions. The white blood cell count in normal blood is 5,000 to 11,000 per microliter (uL) with a lymphocyte value of 20 to 40%, mononuclear cell value of less than 10%, a granulocyte value of 60 to 80%, eosinophil value less than approximately 5% and basophil value less than approximately 2%. The normal range in human blood for red blood cells is 4,000,000 to 5,000,000 cells per microliter. The normal hemoglobin value is 12 to 16 grams/100 ml. The term "hematocrit" is defined as the ratio of volume of packed red blood cells to the volume of whole blood. The normal ratio in humans is about 45%. The mean corpuscular volume is the ratio of the volume of packed red blood cells in ml per liter of blood to red blood cells in millions per microliter. The mean corpuscular hemoglobin concentration is an index indicating the mean or average weight of hemoglobin per 100 ml of packed red blood cells in terms of percent. The mean corpuscular hemoglobin is the ratio of hemoglobin content, in grams per liter, to red blood cells, in millions per microliter.

A control product must accurately indicate on a comparative basis what a test sample of fresh whole blood constitutes with regard to all the above determinations.

While in the foregoing specification, a detailed description of the invention has been set down for the purpose of illustration, many variations in the details herein give may be made by those skilled in the art without departing from the spirit and scope of the invention.

We claim:

1. A hematology control product which contains a leukocyte subpopulation analog comprising a red blood cell that has been treated so that said red blood cell has an increase in volume greater than 50% of its original volume and is resistant to degradation by lytic reagents used in hematological test procedures, and wherein said control product has at least two physical properties of a subpopulation of a human leukocyte, said properties comprising:

a. volume measured by D.C. current, b. high frequency (RF) size, c. opacity, and d. light scatter.

2. The hematology control product of claim 1, wherein one of the two physical properties is light scatter.

3. The hematology control product of claim 1, wherein said control product further comprises the addition of lysable red blood cells.

4. The hematology control product of claim 1, wherein said treated blood cell has a changed hemoglobin content.

5. The hematology control product of claim 4, wherein the hemoglobin of said blood cell had been denatured within the treated blood cell.

6. The hematology control product of claim 4, wherein the hemoglobin of said treated blood cell has been leaked from the treated blood cell.

7. The hematology control product of claim 6, wherein 20% to 80% of the hemoglobin has been leaked from the treated blood cell.

8. The hematology control product of claim 7, wherein said blood cell comprises at least four leukocyte analogs which are distributed within at least four different boundaries of analysis of said instrument, said boundaries of analysis being made on the basis of light scatter, volume and opacity.

9. A method for using a hematology control product which contains a leukocyte subpopulations analog comprising:

a. placing a hematology control product in an instrument, said control product containing a leukocyte subpopulation analog which has been treated so that said red blood cell that has been treated so that said red blood cell has an increase in volume greater than 50% of its original volume and is resistant to degradation by lytic reagents used in hematological test procedures, and wherein said control product simulates has at least two physical properties of a subpopulation of a human leukocyte, said properties comprising:

(1) volume measured by D.C. current,
(2) high frequency (RF) size,
(3) opacity, and
(4) light scatter.

b. measuring said physical properties of the control product; and, c. reporting the results of such measurement in an instrument to determine if said instrument is functioning within specification.

10. The method of claim 9, wherein one of the physical properties is light scatter.

11. The method of claim 9, wherein said leukocyte analog has a changed hemoglobin content.

12. The method of claim 11, wherein said leukocyte analog has 20% to 80% of the hemoglobin leaked from the blood cell.

13. The method of claim 11, wherein the hemoglobin of said leukocyte analog has been denatured in the cell.

14. The method of claim 13, wherein said control product further comprises the addition of lysable red blood cells.

15. The method of claim 14, wherein said leukocyte analog comprises at least four leukocyte analogs which are distributed within at least four different boundaries of analysis of said instrument, said boundaries of analysis being made on the basis of light scatter, volume and opacity.

* * * * *